United States Patent [19]

Fisher et al.

[11] Patent Number: 5,669,770
[45] Date of Patent: Sep. 23, 1997

[54] DENTAL BIB WITH ATTACHED ADHESIVE TAB

[76] Inventors: Sheldon Fisher, 10715 Springdale Ave., Sante Fe Springs, Calif. 90670; Paul Allen Orofino; Richard Allen Orofino, both of 10 Ranick Rd., Hauppauge, N.Y. 11788

[21] Appl. No.: 657,313

[22] Filed: Jun. 3, 1996

[51] Int. Cl.⁶ .................... A41B 13/10; A61C 19/00
[52] U.S. Cl. .................... 433/137; 2/49.1; 604/390
[58] Field of Search ............ 433/137; 604/390; 2/49.1, 49.2, 49.3, 49.4, 49.5; 128/849, 852

[56] References Cited

U.S. PATENT DOCUMENTS

| | | | |
|---|---|---|---|
| 3,488,773 | 1/1970 | Stemmer | 2/52 |
| 4,014,339 | 3/1977 | Tritsch | 604/390 |
| 4,050,121 | 9/1977 | Richman | 604/390 |
| 4,168,196 | 9/1979 | Nemeth et al. | 604/390 |
| 4,645,501 | 2/1987 | Teed | 604/390 |
| 4,660,226 | 4/1987 | Quilling et al. | 2/49.4 |
| 4,704,116 | 11/1987 | Enloe | 604/390 |
| 5,085,655 | 2/1992 | Mann et al. | 604/390 |
| 5,201,727 | 4/1993 | Nakanishi et al. | 604/390 |
| 5,342,685 | 8/1994 | Gobran | 604/390 |
| 5,372,865 | 12/1994 | Arakawa et al. | 604/390 |

*Primary Examiner*—Paul J. Hirsch
*Attorney, Agent, or Firm*—Myron Amer PC

[57] ABSTRACT

A dental bib adhesively secured to a patient in the use of which the adhesive is uncovered incident to use by being unfolded from the bib so that after its use the folding back covers the adhesive so that during disposal there is no inadvertent attachment to a trash container wall, or to trash therein, or like interferences with proper disposal.

1 Claim, 1 Drawing Sheet

U.S. Patent  Sep. 23, 1997  5,669,770
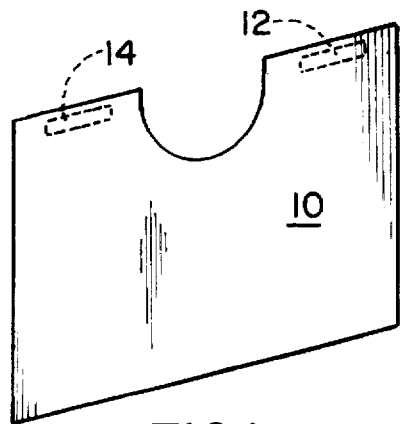
FIG.1 PRIOR ART
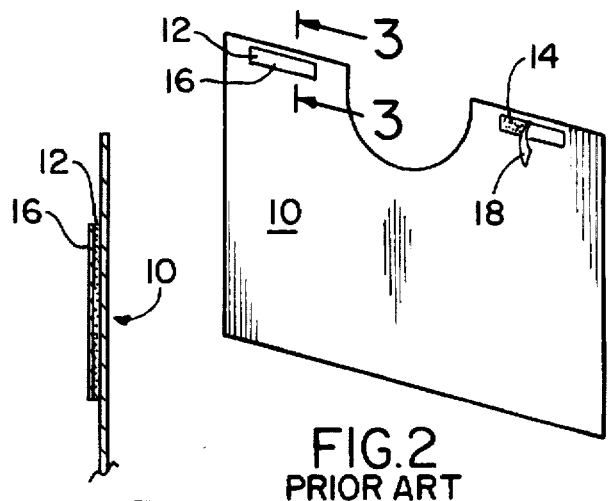
FIG.2 PRIOR ART
FIG.3 PRIOR ART
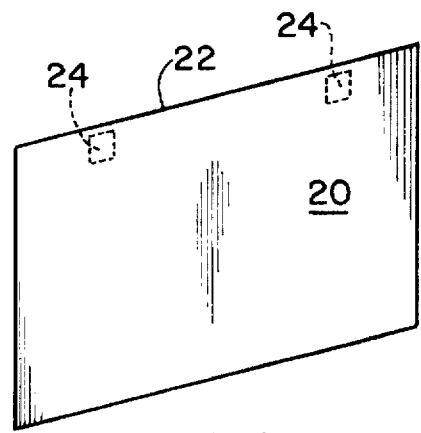
FIG.4
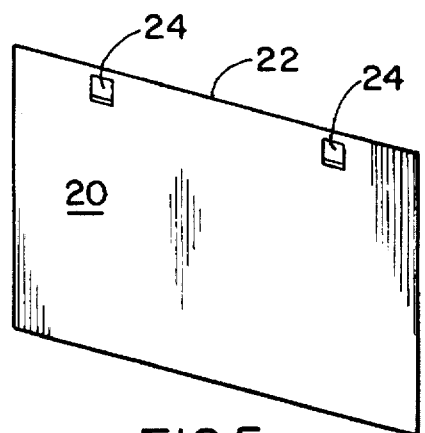
FIG.5
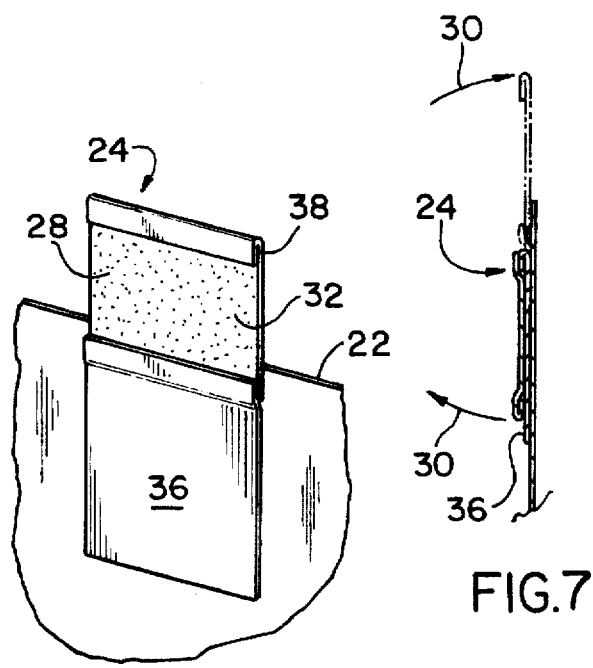
FIG.8
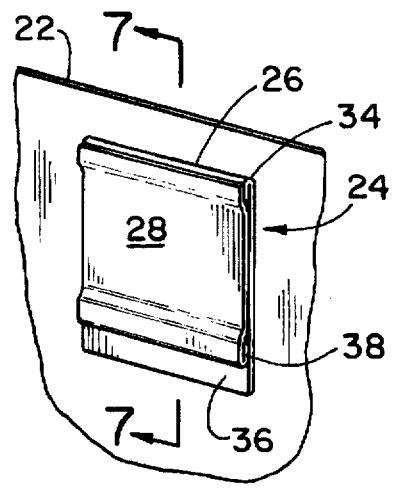
FIG.7
FIG.6

DENTAL BIB WITH ATTACHED ADHESIVE TAB

The present invention relates generally to improvements for adhesively attaching a dental bib or towel to a patient, the improvements more particularly facilitating, after the only one use that is intended for the bib, the effectuating of its disposal.

EXAMPLES OF THE PRIOR ART

Dental bibs eschewing the use of a neck-encircling chain and so-called alligator clip connections to the bib as a means of attachment to a patient and using, instead, deposits of adhesive to establish attachment to a patient, are already well known, as exemplified by U.S. Pat. No. 4,660,226 for "Bib" issued to Quilling et al. on Apr. 28, 1987 and U.S. Pat. No. 3,488,773 for "Dental Towel" issued to S. A. Stemmer on Jan. 13, 1970.

These and all other known adhesively-attached dental bibs preliminary to use of the attaching deposits of adhesive thereon require the removal in covering relation thereover of adhesive-inert release tabs which cannot conveniently be replaced back over the adhesive deposits. In practice, therefore, after use of the bib, it is disposed of with exposed adhesive which inadvertently attaches to surfaces, such as the inside of a disposal container or the like, which interferes with proper disposal, as well as resulting in litter in the form of the removed release tabs.

Broadly, it is an object of the present invention to provide an improved adhesively-attached dental bib overcoming the foregoing and other shortcomings of the prior art.

More particularly, it is an object to embody adhesive means on the dental bib which does not require complete removal of the release tab associated therewith, thereby obviating the littering problem, and facilitating the replacement of the release tab into its covering position over the adhesive means, thereby preparing the bib for convenient disposal, as well as achieving other noteworthy benefits, all as will be better understood as the description proceeds.

FIGS. 1 and 2 are respectively front and rear perspective views of a dental bib having adhesive means for attachment to a patient and subsequently disposed according to prior art practice with the adhesive means exposed;

FIG. 3 is a partial sectional view taken along line 3—3 of FIG. 2;

FIGS. 4 and 5, like FIGS. 1 and 2, similarly are respectively front and rear perspective views of an adhesively-attached dental bib, but of the within inventive embodiment in which disposal after use is with the adhesive means covered;

FIG. 6 is an enlarged scale partial perspective of an adhesive means on the bib of FIGS. 4 and 5 preparatory to the use thereof;

FIG. 7 is a sectional view as taken along line 7—7 of FIG. 6; and

FIG. 8 is a view similar to FIG. 6 but illustrating the adhesive means in its exposed condition incident to patient-attaching use.

The prior art illustrated in FIGS. 1-3 is a dental bib 10 of a known type having adhesive deposits 12 and 14 in left and right corner locations which are exposed for patient-attaching use upon removal of adhesive-inert release tabs 16 and 18. After use, the bib 10 requires disposal since it is designed for the only one use to which it has been put, but in carrying out this prior art disposal practice the exposed adhesive deposits 12 and 14 are a significant problem since they invariably attach to sides of the disposal container, trash in the container and like surfaces and, in addition to inadvertent attachment of the bib 10 during disposal as just described, the removed release tabs 16 and 18 invariably accumulate as litter on the floor and elsewhere in the dentist's office.

The within inventive dental bib, designated 20 in the remaining FIGS. 3-8, overcomes the foregoing disposal problem and other shortcomings of all known prior art bibs, as exemplified by bib 10. To this end, bib 20 has attached adjacent an upper edge 22 and in spaced apart opposite corner locations identically constructed and functioning adhesive-inert rectangular bib-attaching tabs 24, each attached along an end 26 near the bib upper edge 22 and of a selected lengthwise extent extending from the attached end edge 26 inwardly of the bib 20, as best illustrated in the enlarged scale perspective view of FIG. 7. From the folded condition of FIG. 6, an upper length portion serving as an adhesive cover 28 is adapted to be unfolded through movement depicted by the arrows 30 into the condition illustrated in FIGS. 7 and 8, which exposes a previously provided adhesive deposit 32 rearwardly of the cover 28 and thus in facing relation to the patient (not shown) thereby readily facilitating adhesive attachment of the bib 20 to the patient.

It should be appreciated from the just described functioning of the bib-attaching tab 24 that there has been eliminated any use of prior art release tabs 16,18 heretofore causing a litter problem and, most important, that the adhesive deposits are prepared for disposal of the bib 20 by folding the cover 28 along fold line 34 back into covering relation over the adhesive covered length portion 36 which is adhesively attached to an underlying surface of the bib and thus has retained its connected or attached condition to the bib 20.

To facilitate gripping of the adhesive cover 28 a lower edge is advantageously provided with a two-ply folded under configuration as noted at 38.

While the dental bib herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method for preparing for use and disposal a one-patient used dental bib with adhesive means thereon for adhesive attachment to a patient of a type heretofore having said adhesive means incident to the use of said bib exposed for attaching service upon the removal of an adhesive-inert release tab from covering relation over said adhesive means and unavoidably requiring disposal of said adhesive-inert release tab, said method comprising the steps of attaching tabs with adhesive deposits thereon at spaced-apart locations along an upper edge of said bib and in an ascending extending relation therefrom, folding said tabs in a descending pivotal traverse upon tab length portions affixed to said bib to cover said adhesive deposits thereon so as to obviate any inadvertent adhesive attachments by said tabs during handling and storage of said bibs, unfolding said tab to expose said adhesive deposits preparatory to patient use of said bib incident to tab attachment to said patient without removal of release strip means as might contribute to litter accumulation, removing after a one-patient use said bib from said patient for disposal, and folding said tabs again in said descending pivotal traverse to cover said adhesive deposits preparatory to placement in a disposal repository, whereby there is obviated any inadvertent attachment to said disposal repository or any loose debris therein as might result from an uncovered adhesive deposit of said disposed dental bib.

\* \* \* \* \*